US00PP23099P3

(12) United States Plant Patent
Austin

(10) Patent No.: US PP23,099 P3
(45) Date of Patent: Oct. 9, 2012

(54) ***ROSA HYBRIDA* SHRUB PLANT NAMED 'AUSKITCHEN'**

(50) Latin Name: *Rosa hybrida*
Varietal Denomination: AUSkitchen

(75) Inventor: David C. H. Austin, Wolverhampton (GB)

(73) Assignee: David Austin Roses Ltd, Albrighton, Wolverhampton (GB)

( * ) Notice: Subject to any disclaimer, the term of this patent is extended or adjusted under 35 U.S.C. 154(b) by 21 days.

(21) Appl. No.: 13/065,165

(22) Filed: Mar. 14, 2011

(65) Prior Publication Data

US 2012/0096607 P1 Apr. 19, 2012

(30) Foreign Application Priority Data

Oct. 13, 2010 (QZ) ..... PBR 20102157

(51) Int. Cl.
*A01H 5/00* (2006.01)

(52) U.S. Cl. ..... Plt./107; Plt./102

(58) Field of Classification Search ..... Plt./102, Plt./107

See application file for complete search history.

*Primary Examiner* — Susan McCormick Ewoldt

(74) *Attorney, Agent, or Firm* — Kauth, Pomeroy, Peck & Bailey LLP

(57) ABSTRACT

A variety of rose plant of the shrub class, named 'AUSkitchen'. The 'AUSkitchen' rose is a plant suitable for repeat flowering production having flowers with the full-petalled character of an English Rose that are a deep pink, almost red, and that gradually fade to a pure deep pink and are borne on large, pyramidal clusters. The rose is very disease resistant with thick, glossy foliage.

1 Drawing Sheet

Classification: The present invention relates to a new *Rosa hybrida* shrub.

Variety denomination: The new plant has the varietal denomination 'AUSkitchen.'

CROSS-REFERENCE TO RELATED APPLICATIONS

The current application claims priority to a European Community Plant Variety Application No. 2010/2157, filed Oct. 13, 2010, the disclosure of which is incorporated herein by reference.

ORIGIN OF INVENTION

This invention relates to a new and distinct variety of shrub rose plant named 'AUSkitchen', which was originated by crossing two unnamed, unpatented varieties of *Rosa hybrida*.

BACKGROUND OF THE INVENTION

The primary objective of this breeding was to produce a rose that retains the full-petalled character of an English rose, but has an overall character that is quite different. In particular, in this rose breed the young flowers are a deep pink, almost red, gradually fading to a pure deep pink that are borne on large, pyramidal clusters, where the individual blooms open in succession. The rose is also very disease resistant with thick, glossy foliage.

SUMMARY OF THE INVENTION

Among the features which distinguish the new variety from others presently available and commercial rose cultivars known to the inventor is the following combination of characteristics: large pyramidal clusters of blooms which open in succession, thick glossy foliage, compact bushy growth, excellent disease resistance, and double blooms of deep pink, almost red, which fade to deep pink as the flower ages.

Asexual reproduction of the new variety by budding as performed in greenhouses at Bowling Green Lane in Albrighton, Britain shows that the foregoing and other distinguishing characteristics come true to form and are established and transmitted through succeeding asexual propagations. 'AUSkitchen' may be asexually propagated by budding. The budding successfully occurred on the plant/rootstock *Rosa* cv. 'Dr. Huey' in the United States, and *Rosa dumetorum* cv. 'Laxa' for the observed plants in the UK.

COMPARISON WITH PARENTS

The new rose may be distinguished from its seed parent, by the following combination of characteristics: whereas the seed parent has single flowers and broader growth, 'AUSkitchen' is vigorously disease resistant and bears double flowers.

The new variety may be distinguished from its pollen parent, by the following combination of characteristics: whereas the pollen parent is of a lighter pink with smaller cupped flowers and a spreading growth, 'AUSkitchen' has a compact growth and bears blooms of a deeper pink.

COMPARISON WITH THE CLOSEST COMMERCIALLY AVAILABLE CULTIVAR

The closest commercially available cultivar to the new variety is the 'AUSlounge' (co-pending application Ser. No. 13/065,159). The new rose may be distinguished from the 'AUSlounge' variety by the following combination of characteristics: the 'AUSkitchen' produces blooms that are a little larger with more petals than those of 'AUSlounge.' More particularly, the way in which the blooms are held on the plant differs. On 'AUSkitchen' the blooms are held in large pyramidal clusters of 10 to 14 blooms and on 'AUSlounge' they are held in small, flatter clusters of 4 to 6 blooms. In addition, 'AUSkitchen' is a more compact shrub than 'AUSlounge' and the foliage of 'AUSkitchen' is glossier than that of 'AUSlounge.'

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (2001) except where common terms of color definition are employed.

DESCRIPTION OF THE NEW VARIETY

The following description is of 1 year-old rose plants of the new variety grown outdoors in Albrighton, Britain in the month of August. Phenotypic expression may vary with environmental, cultural and climatic conditions, as well as differences in conditions of light and soil.

FLOWER CHARACTERISTICS

Blooming habit: Recurrent. The number of blooms per plant during the growing season is profuse, but there are too many to count.

Bud:

*Size*.—About 2.8 cm long and 1.9 cm in diameter when the petals start to unfurl.

*Form*.—The bud form is pointed ovoid.

*Color*.—When sepals first divide, the bud color is red-purple RHS 63A. When half blown, the upper sides of the petals are red-purple RHS 67A, and the lower sides of the petals are red-purple RHS 64C.

*Calyx*.—Shape: star-shape, folding back. Length: 4 cm. Diameter: 4 cm.

*Sepals*.—Arrangement: Regular, opening to a star shape. Color: Upper Surface: yellow-green RHS 145B. Lower Surface: yellow-green RHS 144B. Length: 2.1 cm. Width: 1 cm. Shape: Lanceolate. Margin: Glandular. Surface texture: Upper Surface: Downy. Lower Surface: Smooth. Number: There are three lightly appendaged sepals. There are 2 unappendaged sepals with glandular edges.

*Receptacles*.—Color: yellow-green RHS 144B. Shape: funnel. Size: small, about 0.9 cm×0.7 cm. Surface: Smooth.

*Peduncle*.—Length: short, averaging about 7 cm. Surface: glandular. Color: yellow-green RHS 144B. Strength: Strong.

Blooms:

*Size*.—Medium, average open diameter is about 9 cm.

*Borne*.—In clusters of 10 to 14 blooms having pyramidal shape.

*Stems*.—Strength: Strong, average length is about 30 cm. Diameter: 6 mm.

*Form*.—When first open, bloom is cupped. Permanence of bloom: outer petals curl back.

Petalage: Number of petals under normal conditions: 85.

*Color*.—The upper sides of the petals are red-purple RHS 67A. The reverse sides of the petals are red-purple RHS 64C, occasional outer petals have some yellow shading RHS 12D emanating from the yellow spot. The base of the petals has a medium yellow spot RHS 9A.

*Variegations*.—N/A.

*Discoloration*.—The general tonality at the end of the first day is red-purple RHS 67A, and at the end of the third day is red-purple RHS 67C. Thereafter, the color fades to red-purple RHS 62B.

*Fragrance*.—Moderate. Character of fragrance: Tea.

Petals:

*Texture*.—Thick.

*Size*.—Width: 2.9 cm. Length: 4 cm.

*Surface*.—Smooth.

*Shape*.—Obovate.

*Margin*.—Some entire and some notched.

*Apex shape*.—Rounded.

*Base shape*.—Pointed.

*Form*.—Incurved.

*Arrangement*.—Imbricated.

*Petaloids*.—Number: About 9. Color: red-purple RHS 64C. Length: Variable 9 mm to 1.9 cm. Width: Variable 3 mm to 8 mm. Shape: Variable. Margin: Irregular.

*Persistence*.—Petals drop off cleanly before drying.

*Lastingness*.—On the plant: Fair, about 5 days. As a cut flower: Not tested.

Reproductive parts:

*Stamens*.—Number: 40. Length: 5 mm.

*Anthers*.—Length: 1.5 mm. Color: yellow-orange RHS 15A. Arrangement: Regular around styles.

*Filaments*.—Color: yellow-orange RHS 15A. Length: 4 mm.

*Pollen*.—Color: greyed-orange RHS 163A.

*Pistils*.—Number: 30. Length: 6 mm.

*Styles*.—Color: green-yellow RHS 1D. Length: 3 mm.

*Stigmas*.—Color: yellow RHS 2D. Length: 3 mm.

*Hips*.—None Observed.

PLANT CHARACTERISTICS

Plant form: Shrub.

Plant growth: Compact and bushy.

Age to maturity: Two years.

Mature plant: Height: 90 cm. Width: 70 cm.

Rootstock: *Rosa* cv. 'Dr. Huey' in the United States, *Rosa dumetorum* cv. 'Laxa' for the observed plants in the UK.

Foliage:

*Number*.—Leaflets on normal mid-stem leaves is: 5 (including terminal leaflet).

*Size*.—Medium, about 12 cm long×9 cm wide.

*Quantity*.—Abundant. Number of leaves per flowering stem is: 10.

*Color*.—New foliage: Upper side: yellow-green RHS 144A tinged with red-purple RHS 59B. Lower side: yellow-green RHS 144A tinged with red-purple RHS 59B. Old foliage: Upper side: green RHS 137A. Lower side: green RHS 138A.

Leaflets:

*Size*.—About 5 cm long×4 cm wide.

*Shape*.—Broadly oval.

*Base shape*.—Rounded.

*Apex shape*.—Acuminate.

*Texture*.—Glossy.
*Edge*.—Serrated.
*Serrations*.—Single.
*Petiole*.—Color: green RHS 138A tinged with red-purple RHS 59B. Length: 3.2 cm. Width: 2 mm. Surface Texture: Smooth.
*Petiole rachis*.—Color: green RHS 138A, tinged with red-purple RHS 59B. Underside: with prickles.
*Stipules*.—Length: 1.5 cm, glandular. Color: green RHS 138A.
*Auricle*.—Shape: Sword shaped. Length: 3 mm. Width: 1.5 mm. Color: green RHS 138A.
*Vein color*.—Green RHS 137A.
*Venation pattern*.—Reticulate.

Wood:
*New wood*.—Color: green RHS 138A. Bark: Smooth.
*Old wood*.—Color: green RHS 138A. Bark: Smooth.

Branching habit:
*Number*.—8.
*Lateral branch dimensions*.—Length: 40 cm. Width: 6 mm.

Stems:
*Mature stem*.—Length: 80 cm. Diameter: 7 mm.
*Internode distance*.—9 cm. The above measurements are all variable, depending on growing conditions in a season.
*Stem pubescence present*.—No.

Prickles:
*Quantity*.—On main canes from base: Many. Number per stem length: 30 per 10 cm. On laterals from main canes: Many. Number per stem length: 30 per 10 cm.
*Form*.—Deep concave.
*Length*.—9 mm (also 1 mm to 3 mm small prickles).
*Color when young*.—Greyed-purple RHS 183A.
*Color when mature*.—Greyed-purple RHS 183A and green RHS 138A.

Small prickles:
*Quantity*.—Main stalk: Many. Number per stem length: 30 per 10 cm. Laterals: Many. Number per stem length: 30 per 10 cm.
*Color*.—When young: greyed-purple RHS 183A. When mature: greyed-purple RHS 183A.

Disease resistance:
*Mildew*.—Resistant.
*Blackspot*.—Resistant.
*Rust*.—Resistant.

Pest resistance: Not tested.
Winter hardiness: Not tested.
Growing conditions: Normal.

What is claimed is:

1. A new and distinct variety of rose plant of the shrub class suitable for repeat flower production, substantially as herein shown and described.

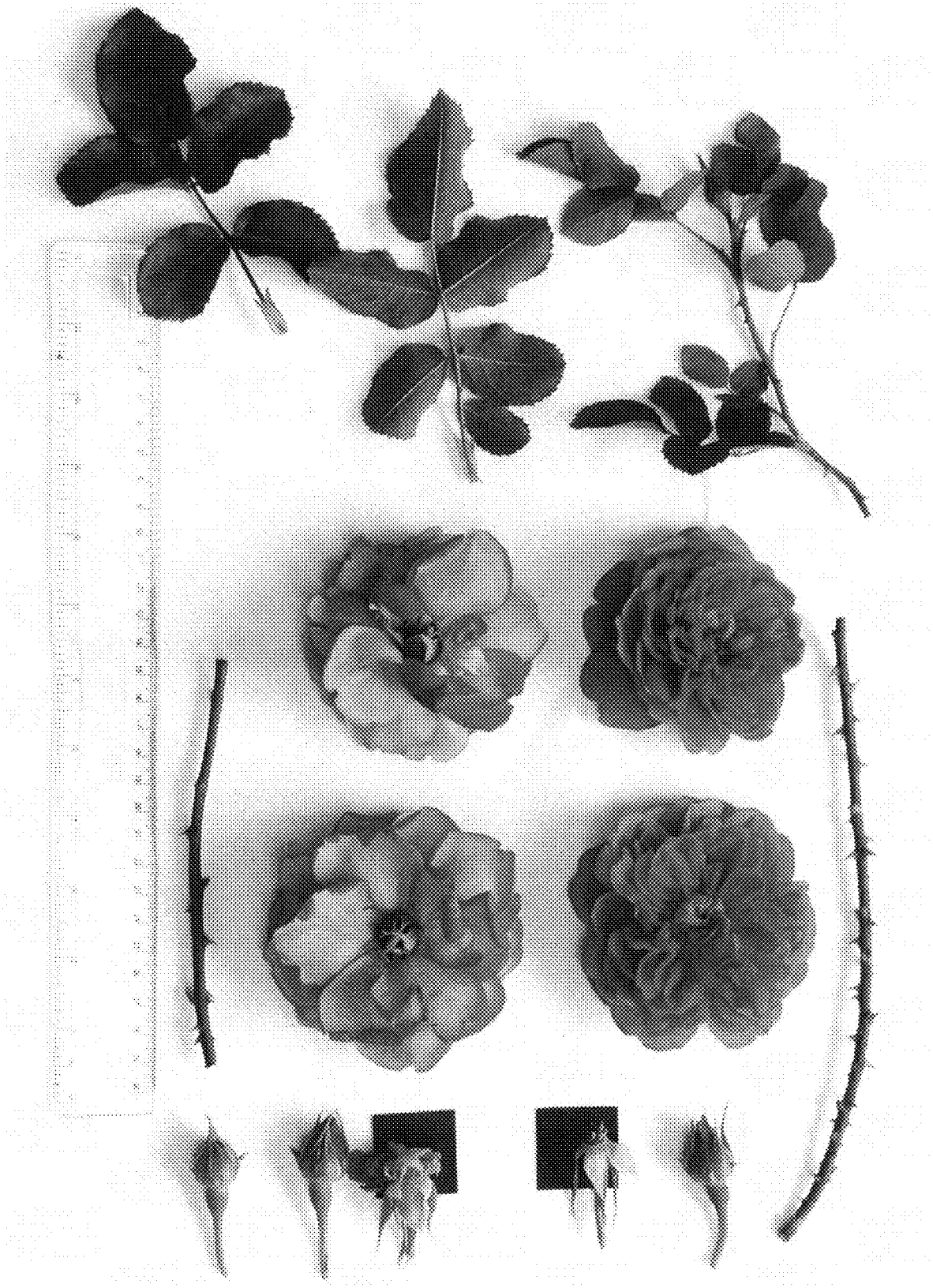

* * * * *